US 9,426,980 B2

(12) United States Patent
Tousimis (10) Patent No.: US 9,426,980 B2
(45) Date of Patent: Aug. 30, 2016

(54) **CRITICAL POINT DRYING SYSTEMS AND METHODS FOR *IN SITU* TISSUE PRESERVATION**

(71) Applicant: Anastasios J. Tousimis, North Bethesda, MD (US)

(72) Inventor: Anastasios J. Tousimis, North Bethesda, MD (US)

( * ) Notice: Subject to any disclaimer, the term of this patent is extended or adjusted under 35 U.S.C. 154(b) by 0 days.

(21) Appl. No.: 14/686,058

(22) Filed: Apr. 14, 2015

(65) Prior Publication Data

US 2015/0216162 A1    Aug. 6, 2015

Related U.S. Application Data

(62) Division of application No. 14/336,560, filed on Jul. 21, 2014, now Pat. No. 9,027,213, which is a division of application No. 14/039,733, filed on Sep. 27, 2013, now abandoned, which is a division of application No. 13/695,790, filed as application No. PCT/US2012/026316 on Feb. 23, 2013, now Pat. No. 8,563,234.

(51) Int. Cl.
*A01N 1/00*  (2006.01)
*A01N 1/02*  (2006.01)
*A61L 2/00*  (2006.01)
*A61L 9/00*  (2006.01)

(52) U.S. Cl.
CPC ............ *A01N 1/0252* (2013.01); *A01N 1/00* (2013.01); *A01N 1/021* (2013.01); *A01N 1/0247* (2013.01)

(58) Field of Classification Search
CPC ...... A01N 1/0252; A01N 1/00; A01N 1/021; A01N 1/0247

USPC .......................................... 27/22.1; 422/295
See application file for complete search history.

(56) References Cited

U.S. PATENT DOCUMENTS

| | | | |
|---|---|---|---|
| 2,106,261 | A | 1/1938 | Weidemann |
| 3,408,712 | A | 11/1968 | Pauliukonis et al. |
| 3,782,382 | A | 1/1974 | Naftulin et al. |
| 3,912,809 | A | 10/1975 | Rendon |
| 4,104,808 | A | 8/1978 | Horne et al. |
| 4,205,059 | A | 5/1980 | von Hagens |
| 4,278,701 | A | 7/1981 | von Hagens |

(Continued)

OTHER PUBLICATIONS

Alpar et al., "Plastination of pathological specimens—a continuing challenge," Journal of the International Society for Plastination, 2005, 20: pp. 8-12.

(Continued)

*Primary Examiner* — Tatyana Zalukaeva
*Assistant Examiner* — Andrew J Mensh
(74) *Attorney, Agent, or Firm* — Shapiro, Gabor and Rosenberger, PLLC (57) ABSTRACT

Methods and systems for preserving tissues in situ using critical point drying are disclosed. Such methods and systems are particularly applicable to the preservation of a deceased body, such as a deceased person or animal, with or without removal of internal tissues or organs. A fixative can be perfused through the vascular system of the body while blood is removed from the body. The exterior of the body can also be immersed in a bath of fixative. The fixative in the vascular system and the bath can be replaced by subsequent washes of buffer, de-ionized water, and/or alcohol. The alcohol-infused and fixated body can be disposed in a pressure chamber and subjected to a critical point drying process using carbon dioxide. After the critical point drying process, the body is in a preserved state.

12 Claims, 8 Drawing Sheets

(56) References Cited

U.S. PATENT DOCUMENTS

| | | | |
|---|---|---|---|
| 4,320,157 A | 3/1982 | von Hagens | |
| 4,784,873 A | 11/1988 | Kienecker et al. | |
| 5,300,540 A | 4/1994 | Masters | |
| 5,350,670 A | 9/1994 | Yeh | |
| 5,405,606 A | 4/1995 | Campbell et al. | |
| 5,431,952 A | 7/1995 | Ocello | |
| 5,607,668 A | 3/1997 | Campbell et al. | |
| 5,622,695 A | 4/1997 | Campbell et al. | |
| 5,622,696 A | 4/1997 | Camiener | |
| 5,715,583 A * | 2/1998 | Sandoval | A01N 1/00 27/11 |
| 5,827,511 A | 10/1998 | Campbell et al. | |
| 6,042,874 A | 3/2000 | Visinoni et al. | |
| 6,493,964 B1 | 12/2002 | Tousimis et al. | |
| 6,678,968 B1 | 1/2004 | Tousimis et al. | |
| 6,857,200 B1 | 2/2005 | Tousimis et al. | |
| 7,008,591 B2 | 3/2006 | Kafesjian et al. | |
| 7,257,871 B2 | 8/2007 | Aoyagi et al. | |
| 2010/0030340 A1 | 2/2010 | Wolfinbarger et al. | |
| 2010/0196996 A1* | 8/2010 | Kilic | A01N 1/00 435/260 |

OTHER PUBLICATIONS

Marks et al., "Plastinated tissue samples as three-dimensional models for optical instrument characterization," Opt. Express, Sep. 2008, 16(20): pp. 16272-283.

Mayer et al., "Embalming: History, Theory, & Practice," Third Edition, New York, McGraw-Hill, 2000, pp. 103-141, 157-177, and 241-273. RA623.M385 2000.

Summum®, "Eternal Memorialization through Mummification," Brochure [online] [retrieved on Jun. 12, 2012]. Retrieved from the Internet: <URL: http://www.summum.org/mummification/EternalMemorialization-hi.pdf>.

\* cited by examiner

CRITICAL POINT DRYING SYSTEMS AND METHODS FOR *IN SITU* TISSUE PRESERVATION

CROSS-REFERENCE TO RELATED APPLICATIONS

The present application is a divisional of U.S. application Ser. No. 14/336,560, filed Jul. 21, 2014, which is a divisional of U.S. application Ser. No. 14/039,733, filed Sep. 27, 2013, which is a divisional of U.S. application Ser. No. 13/695,790, filed Nov. 1, 2012, now U.S. Pat. No. 8,563,234, which is a U.S. national stage of International Application No. PCT/US12/26316, filed Feb. 23, 2012, all of which are hereby incorporated by reference herein in their entireties.

FIELD

The present disclosure relates generally to the preservation of tissues, and, more particularly, to the preservation of tissues in situ using critical point drying.

SUMMARY

In general, perfusion of fixative together with critical point drying can be used to preserve a body, such as a deceased human or animal, without removal of internal tissues or organs. Fixative can be perfused through the vascular system of the body through the heart while blood is removed from the body. The exterior of the body can also be immersed in a bath of fixative. The fixative can be replaced by subsequent washes of buffer, de-ionized water, and/or alcohol. The body can be infused with and immersed in, for example, liquid carbon dioxide. Critical point drying of the body can then be performed by heating to a temperature and pressure at or in excess of the critical point (i.e., the critical temperature and pressure) of carbon dioxide. The carbon dioxide can then be exhausted, after which the body remains in a substantially preserved state. In one or more alternative embodiments, critical point drying alone (i.e., without any fixation) may be used to preserve certain bodies and/or tissues.

In one or more embodiments, a method for preserving a deceased body or an organ thereof can include perfusing the body or the organ with fixative delivered via the vascular system thereof. After the perfusing with fixative, the body or the organ can be perfused with liquid carbon dioxide delivery via the vascular system thereof. After the perfusing with liquid carbon dioxide, the body or the organ can be heated in a sealed chamber until the temperature and pressure in the chamber meets or exceeds the critical point for carbon dioxide.

In one or more embodiments, a system for preservation of a body or an organ thereof can include a pressure chamber having at least one fluid inlet and a vascular inlet line. The vascular inlet line can connect to the vascular system of the body or the organ. The pressure chamber can be sized and shaped so as to allow the body or the organ to be enclosed therein. A flow module can supply at least a transitional fluid to the pressure chamber through the at least one fluid inlet and to the vascular system through the vascular inlet line. For example, the transitional fluid can be carbon dioxide. A temperature module can control the temperature of the pressure chamber. A system controller can control the flow module to fill the pressure chamber and the vascular system with transitional fluid. The system controller can additionally control the temperature module to heat the transitional fluid above its critical point temperature and to pressurize the transitional fluid above its critical point pressure. The pressure chamber can be constructed to withstand at least the critical point temperature and pressure of the transitional fluid.

In one or more embodiments, a method for preserving a body or an organ thereof can include perfusing the body or the organ with liquid carbon dioxide by way of the vascular system while the body or the organ is in a sealed pressure chamber. The external surfaces of the body or the organ can be exposed to liquid carbon dioxide while the body is in the sealed pressure chamber. The body or the organ can be heated in the sealed pressure chamber until the temperature and pressure in the pressure chamber meets or exceeds the critical point for carbon dioxide. The method can further include, after the heating, exhausting carbon dioxide from the pressure chamber and the body or the organ therein.

In one or more embodiments, a method for preserving a recently deceased human body can include connecting a perfusion inlet and outlet to the vascular system of the deceased human body. The method can further include flowing a fixative into the vascular system of the deceased human body and immersing the deceased human body in fixative. The fixative can include, for example, glutaraldehyde or formaldehyde. The method can also include flowing a buffer solution into the vascular system and immersing the deceased human body in buffer solution. In addition, the method can include flowing water into the vascular system and immersing the deceased human body in water. The method can include flowing alcohol into the vascular system and immersing the deceased human body in alcohol. The method can additionally include flowing liquid carbon dioxide into the vascular system and immersing the deceased human body in liquid carbon dioxide in a sealed pressure chamber. Further, the method can include heating the deceased human body in the sealed pressure chamber until the temperature and pressure in the pressure chamber meets or exceeds the critical temperature and critical pressure for carbon dioxide.

Objects and advantages of the present disclosure will become apparent from the following detailed description when considered in conjunction with the accompanying drawings.

BRIEF DESCRIPTION OF DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

To arrest the decay and decomposition of a recently deceased body, the cells of the body can be exposed to a fixative. The exterior of the body is immersed or submerged in the fixative. Cells internal to the body can be exposed to the fixative by perfusing the fixative through the vascular system. In other words, fixative may be flowed through the circulatory system. Access to the vascular system may be achieved by an appropriate incision to the thoracic cavity and coupling perfusion tubing to the heart. Perfusion of fluids into the deceased body may also be accomplished via an arterial connection or other access point, such as, but not limited to a fistula, a graft, or a catheter.

Fixative internal and external to the body can be sequentially replaced by subsequent washes of buffer, water, and/or alcohol. With the body in a pressure chamber, the alcohol can be replaced with a critical point drying agent, such as but not limited to carbon dioxide. Critical point drying of the body can be performed by heating the pressure chamber and the body therein past the critical point (i.e., the critical temperature and pressure) of the drying agent and then exhausting the drying agent from both the body and the chamber. In alternative embodiments, critical point drying alone may be used to preserve certain bodies or tissues, such as, but not limited to, vegetation and non-vascular organisms.

According to embodiments of the systems, methods, and devices disclosed herein, a deceased body may be preserved indefinitely. The cellular structure of the body can be maintained, thereby allowing diagnostic or anatomical analysis, such as for medical training or research. Because the decomposition has been arrested, the deceased body may be maintained indefinitely in the same condition as it was immediately post-mortem. In addition, cellular material and structure are preserved by the fixation process. Future technological advances may thus be able reverse the fixation process and reanimate the deceased body.

In embodiments, the systems, methods, and devices described herein can be applied to the long-term preservation of recently deceased humans, as an alternative to conventional embalming and/or cryonics processes. Although certain examples are explicitly discussed herein with respect to deceased humans, the methods, systems, and devices are equally applicable to the preservation of a wide range of biological organisms and structures, including, but not limited to, deceased animals, insects, and plants, as well as tissues, organs, and portions thereof.

Figure 1:
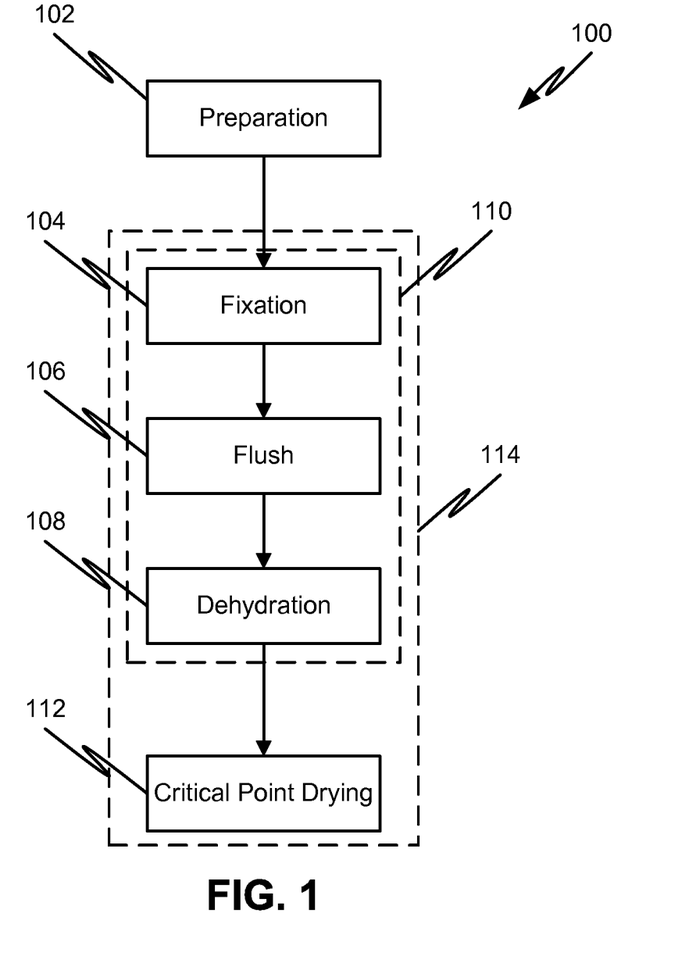
FIG. 1 is a schematic diagram showing generalized features of a method for in situ tissue preservation according to one or more embodiments of the disclosed subject matter.

Referring now to FIG. 1, a generalized method 100 for in situ tissue preservation is shown. The method 100 can begin with an optional preparation step 102. In the optional preparation step 102, the body may be cleansed in preparation for fixation, such as by washing and/or disinfecting the exterior of the body. Certain interior cavities of the body may also be cleansed. For example, an enema or colonic may be performed to remove fecal matter, bacteria, gut flora, and/or other foreign organisms from the lower gastrointestinal tract. Undigested or partially digested food may also be removed from the upper gastrointestinal tract. However, such a step 102 is not required and may be omitted.

In addition, the preparation may include repairing damage to the vascular system. In some circumstances, the deceased body may have undergone damage due to, for example, an accident, trauma, autopsy, injury, or other occur occurrence. In such circumstances, the damage can be surgically repaired to allow perfusion through the vascular system. Alternatively, the damage can be sealed or bypassed with appropriate tubing. In still another alternative, the body may be perfused using multi-point injections, for example, using separating injections point in the iliac or femoral arteries, the subclavian or axillary vessels, and/or the common carotids. The preparation at 102 can include making the necessary fluid connections to these injection sites in preparation for later perfusion.

At 104, the body can undergo fixation (e.g., via perfusion) by introducing a fixative into the body and over the external surfaces of the body. Various fixatives can be used to achieve the fixation. For example, the fixative can be 1.5% glutaraldehyde in a phosphate buffer. In another example, the fixative can include a combination of fixatives, such as 1.5% glutaraldehyde and 1% formaldehyde in a buffer solution at a pH of approximately 7.3. For certain applications, impurities in the fixative may adversely affect cell structure or preservation properties. Thus, the fixative may be purified prior to use. While the fixation step 104 may enhance the preservation effect in some application, it can be omitted in other applications. For example, fixation may not be necessary when preserving certain organisms, such as vegetation.

At 106, the fixative can be flushed by one or more washes. Thus, the fixative and remnants thereof can be removed from the body in preparation for subsequent critical point drying. The flushing step 106 can be achieved using multiple washes of buffer and/or water. For example, a buffer can be perfused through and flowed over the body for a sufficient volume to allow complete removal of the fixative, after which water can then be perfused through and flowed over the body for a sufficient volume to allow complete removal of the buffer. Alternatively, a sufficient volume of buffer can be introduced to completely fill the body's vascular system and to completely cover the body. After a dwell period, the buffer can be replaced with fresh buffer. This can be repeated one or more times, for example, a total of three buffer baths, before the buffer is replaced with water. As with the buffer, the water can be introduced to completely fill the body's vascular system and to completely cover the body. After a dwell period, the water can be replaced with fresh water. This may be repeated one or more times, for example, a total of three water baths.

At 108, the body can be dehydrated by replacing the water with an alcohol. When critical point drying 112 is performed using carbon dioxide, dehydration 112 is necessary since carbon dioxide is generally immiscible in water. The water thus must be replaced with a miscible fluid, e.g., an alcohol, in order for the critical point drying to be effective. As with the buffer and water, the alcohol can be perfused through and flowed over the body for a sufficient volume to allow complete removal of the water. Alternatively, a sufficient volume of alcohol can be introduced to completely fill the body's vascular system and to completely cover the body. After a dwell period, the alcohol can be replaced with fresh alcohol. This may be repeated one or more times, for example, for a total of three alcohol baths.

At 112, liquid carbon dioxide (LCO$_2$) can be introduced to replace the alcohol in and around the body. The body can be placed in a pressure chamber filled with alcohol, after which the liquid carbon dioxide can be introduced at a low temperature. After the liquid carbon dioxide replaces the alcohol in the chamber and the body, the chamber can be heated until the temperature and the pressure in the chamber is at or exceeds the critical point of carbon dioxide, i.e., a temperature of 31° C. and a pressure of 1072 psi. Such temperatures and pressures can be attained without sustaining damage to the cell structure and integrity.

The fixation step 104, flushing step 106, and dehydration step 108 may be incorporated into a common setup 110. The combined fixation/flushing/dehydration setup (such as that shown in FIGS. 3-4) can be separate from the critical point drying step 112 such that the critical point drying step 112 is performed using a different apparatus (such as that shown in FIGS. 5A-5B). The fixation step 104, flushing step 106, dehydration step 108, and critical drying step 112 can also be incorporated together into a common setup 114, such as that shown in FIG. 6 or FIGS. 7A-7C.

Figure 2A:
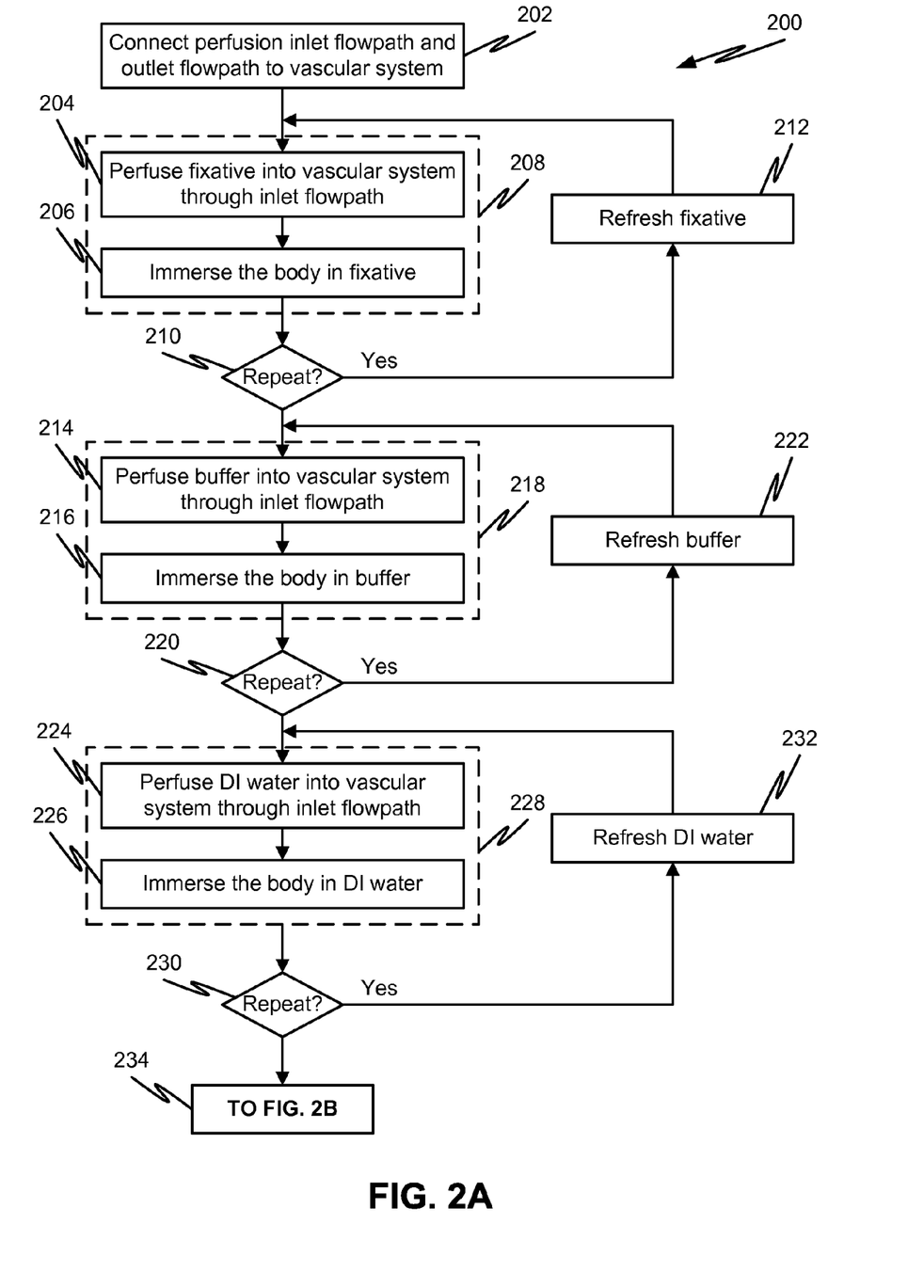
FIGS. 2A-2B is a process flow diagram of a method for in situ tissue preservation according to one or more embodiments of the disclosed subject matter.
Figure 2B:
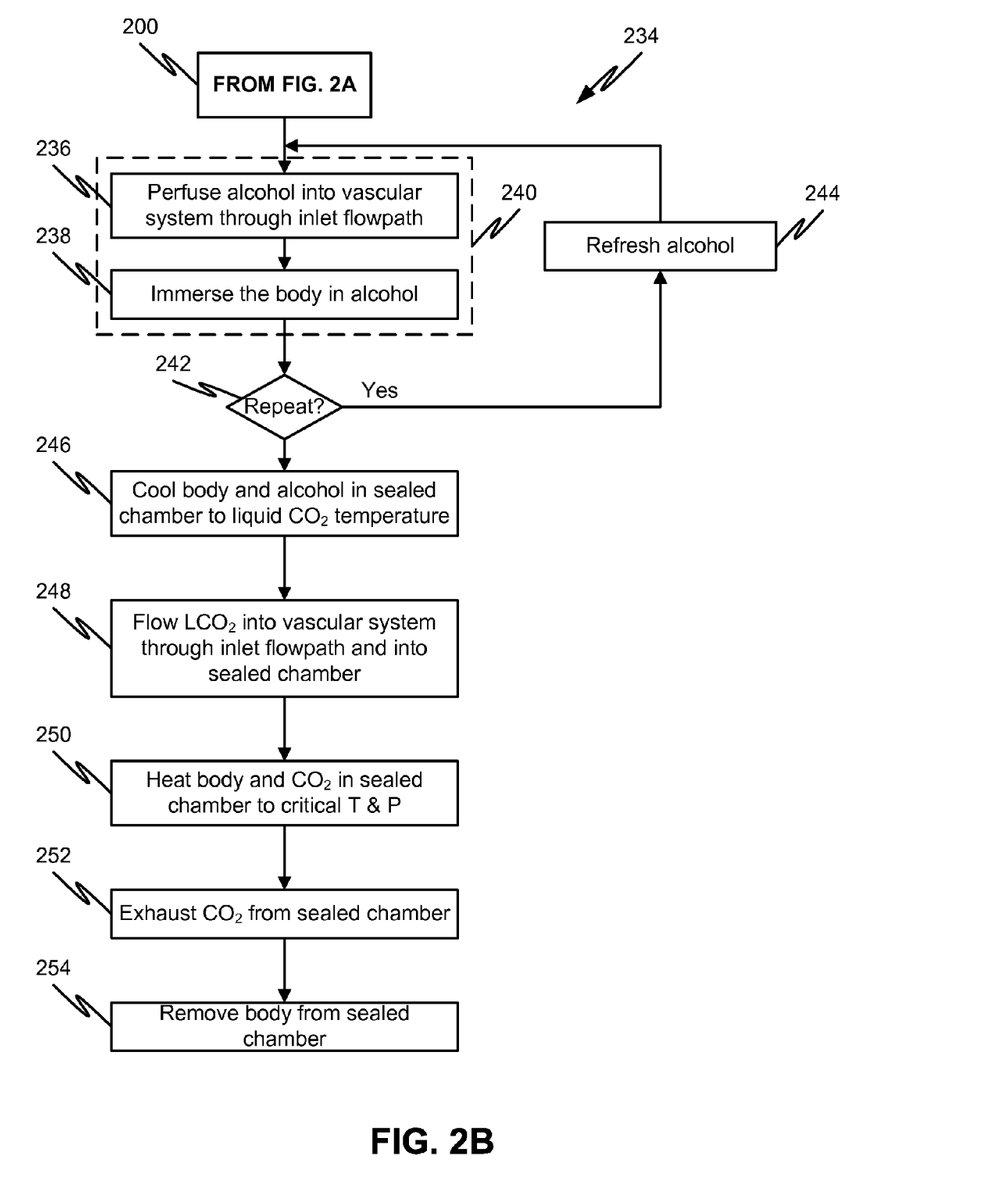

Referring now to FIGS. 2A-2B, an example of a detailed process flow for preservation of a body is shown. Beginning with FIG. 2A, the process of block 200 begins at 202, where an inlet flow path and an outlet flow path are connected to the vascular system of the body. The flow paths can include tubing and/or fluid conduits designed to carry fixative and potentially other fluids, such as buffer, water, alcohol, and liquid carbon dioxide, to the vascular system of the body. For example, the tubing can have a diameter between 0.25 inches and 0.5 inches.

At 204, the inlet and outlet flow paths can be used to perfuse fixative into the vascular system. For example, a fixative can be infused through the inlet flow path, while the contents of the vascular system are drained through the outlet flow path. The fixative can be 1.5% glutaraldehyde in a phosphate buffer or a combination of glutaraldehyde and formaldehyde in a buffer, for example. Perfusion of the fixative can be accomplished, for example, using low pressure pumping or gravity induced flow. In applications where preservation of cell structure may be less important, moderate pressure pumping can be used to reduce infusion and processing times. At least initially, blood will be conveyed out of the vascular system through the outlet flow path. The infusion of fixative continues until the contents of the vascular system are completely replaced with fixative. The fixative can be maintained in the vascular system for a predetermined period of time sufficient to result in fixation of the internal cells of the body. For example, the predetermined period of time can be one to several days, such as three days. The precise time may be a function of the size of the body, as well as other factors, and thus may be subject to variation.

At 206, the body can be immersed in a bath of fixative for a predetermined period of time. For example, the predetermined period of time can be one to several days, such as three days. Steps 204 and 206 can be combined into a single step 208 such that the body is immersed in the bath of fixative at the same time that fixative flows through the vascular system. In such case, the predetermined period of time for both steps 204 and 206 can be the same. It is also noted that steps 204 and 206 can be transposed such that step 206 occurs before step 204.

It may be advantageous to renew the fixative within and in contact with the body. Thus, steps 204 and 206 can be repeated several times (e.g., three times), each time with a new batch of fixative maintained within and in contact with the body for a predetermined time period (e.g., one day). At 210, it is determined if steps 204 and 206 should be repeated. If it is determined that the fixation should be repeated, the process proceeds to 212, where a new batch of fixative is prepared, and steps 204 and 206 are then repeated. Otherwise, the process proceeds to 214.

At 214, the inlet and outlet flow paths can be used to perfuse buffer into the vascular system. For example, a buffer, such as phosphate buffer, can be infused through the inlet flow path, while the contents of the vascular system are drained through the outlet flow path. At least initially, fixative will be conveyed out of the vascular system through the outlet flow path. The infusion of buffer continues until the contents of the vascular system are completely replaced with buffer. The buffer can be maintained in the vascular system for a predetermined period of time. For example, the predetermined period of time can be between one and two hours. The precise time may be a function of the size of the body, as well as other factors, and thus may be subject to variation.

At 216, the body can be immersed in a bath of buffer for a predetermined period of time. For example, the predetermined period of time can be one to two hours. Steps 214 and 216 can be combined into a single step 218 such that the body is immersed in the bath of buffer at the same time that buffer flows through the vascular system. In such case, the predetermined period of time for both steps 214 and 216 can be the same. It is also noted that steps 214 and 216 can be transposed such that step 216 occurs before step 214.

It may be advantageous to renew the buffer within and in contact with the body. Thus, steps 214 and 216 can be repeated several times (e.g., three times), each time with a new batch of buffer maintained within and in contact with the body for a predetermined time period (e.g., 1.5 hours). At 220, it is determined if steps 214 and 216 should be repeated. If it is determined that the buffer flush should be repeated, the process proceeds to 222, where a new batch of buffer is prepared, and steps 214 and 216 are then repeated. Otherwise, the process proceeds to 224.

At 224, the inlet and outlet flow paths can be used to perfuse water into the vascular system. For example, purified water, such as deionized (DI) water or distilled water, is infused through the inlet flow path, while the contents of the vascular system are drained through the outlet flow path. At least initially, buffer will be conveyed out of the vascular system through the outlet flow path. The infusion of water continues until the contents of the vascular system are completely replaced with water. The water can be maintained in the vascular system for a predetermined period of time. For example, the predetermined period of time can be between one and two hours. The precise time may be a function of the size of the body, as well as other factors, and thus may be subject to variation.

At 226, the body can be immersed in a bath of water for a predetermined period of time. For example, the predetermined period of time may be one to two hours. Steps 224 and 226 can be combined into a single step 228 such that the body is immersed in the bath of water at the same time that water flows through the vascular system. In such case, the predetermined period of time for both steps 224 and 226 can be the same. It is also noted that steps 224 and 226 can be transposed such that step 226 occurs before step 224.

It may be advantageous to renew the water within and in contact with the body. Thus, steps 224 and 226 can be repeated several times (e.g., three times), each time with a new batch of water maintained within and in contact with the body for a predetermined time period (e.g., 1.5 hours). At 230, it is determined if steps 224 and 226 should be repeated. If it is determined that the water flush should be repeated, the process proceeds to step 232, where a new batch of water is prepared, and steps 224 and 226 are then repeated. Otherwise, the process proceeds to the process of block 234 in FIGS. 2A-2B.

Referring now to FIG. 2B, the process proceeds from block 200 to 236. At 236, the inlet and outlet flow paths can be used to perfuse an alcohol into the vascular system. For example, an alcohol, such as isopropyl alcohol (IPA) or ethanol, can be infused through the inlet flow path, while the contents of the vascular system are drained through the outlet flow path. At least initially, water will be conveyed out of the vascular system through the outlet flow path. The infusion of alcohol continues until the contents of the vascular system are completely replaced with alcohol. The alcohol can be maintained in the vascular system for a predetermined period of time. For example, the predetermined period of time can be between one and several days, such as one day. The precise time may be a function of the size of the body, as well as other factors, and thus may be subject to variation.

At 238, the body can be immersed in a bath of alcohol for a predetermined period of time. For example, the predetermined period of time can be between one and several days. Steps 236 and 238 can be combined into a single step 240 such that the body is immersed in the bath of alcohol at the same time that alcohol flows through the vascular system. In such case, the predetermined period of time for both steps 236 and 238 can be the same. It is also noted that steps 236 and 238 can be transposed such that step 238 occurs before step 236.

It may be advantageous to renew the alcohol within and in contact with the body. Thus, steps 236 and 238 can be repeated several times (e.g., three times), each time with a new batch of alcohol maintained within and in contact with the body for a predetermined time period (e.g., one day). At step 242, it is determined if steps 236 and 238 should be repeated. If it is determined that the dehydration with alcohol should be repeated, the process proceeds to step 244, where a new batch of alcohol is prepared, and steps 224 and 226 are then repeated.

At 246, the body and alcohol can be cooled in a sealed chamber to a first predetermined temperature, at which a transitional fluid exists as a liquid, in preparation for critical point drying. When steps 204-238 are performed using an apparatus separate from a critical point drying apparatus, the body can be transferred to the chamber in a bath of alcohol and sealed to prevent reintroduction of water. The transitional fluid can be, for example, carbon dioxide, in which case the sealed chamber is cooled to a temperature less than or equal to 10° C. The pressure can be maintained substantially at atmospheric pressure.

At 248, the inlet flow path is used to perfuse transitional fluid into the vascular system. A common or separate inlet in the sealed chamber can be used to convey transitional fluid into the sealed chamber so as to replace the alcohol in and surrounding the body. For example, transitional fluid, such as liquid carbon dioxide, can be simultaneously infused through the inlet flow path and introduced into the sealed chamber. The contents of the vascular system can be drained through the outlet flow path. Since the body is located in a sealed chamber, the outlet flow path can empty directly into the sealed chamber, or alternatively, be connected to an outlet of the sealed chamber for removal. An outlet in the sealed chamber may serve to remove the fluid contents of the sealed chamber as fluid is added thereto.

The infusion of liquid carbon dioxide can continue at least until the contents of the vascular system are completely replaced with liquid carbon dioxide. The liquid carbon dioxide can be maintained in the sealed chamber and the vascular system for a predetermined period of time. Alternatively, the liquid carbon dioxide can be continuously flowed through the sealed chamber and the vascular system for a predetermined period of time. For example, the predetermined period of time can be between ten minutes and one hour. The precise time may be a function of the size of the body, as well as other factors, and thus may be subject to variation. During the infusion of liquid carbon dioxide, the chamber and the body therein can be maintained at or below 10° C.

At 250, the flow of liquid carbon dioxide through the sealed chamber and vascular system can be stopped such that the sealed chamber and vascular system are filled with liquid carbon dioxide. The body and the carbon dioxide in the sealed chamber can then be heated to or beyond the critical point. The critical point for carbon dioxide occurs at a temperature of approximately 31° C. and a pressure of approximately 1072 psi. At the critical point, the density of the liquid and gas phases are identical such that the carbon dioxide can be exhausted without damage to the cell structure of the body.

At 252, the pressurized carbon dioxide in the sealed chamber can be removed. Because of the relatively high pressure, the carbon dioxide can be slowly vented from the sealed chamber while maintaining the temperature above 31° C. to avoid condensation of the carbon dioxide. For example, the chamber can be vented such that the carbon dioxide is exhausted at a rate of between 8 standard $ft^3$ per hour (SCFH) and 10 SCFH. At pressures below 400 psi, for example, the exhaust rate can be increased, if so desired. When the pressure in the sealed chamber is substantially equal to atmospheric pressure, the process proceeds to 254, wherein the preserved body can be removed from the sealed chamber.

Figure 3:
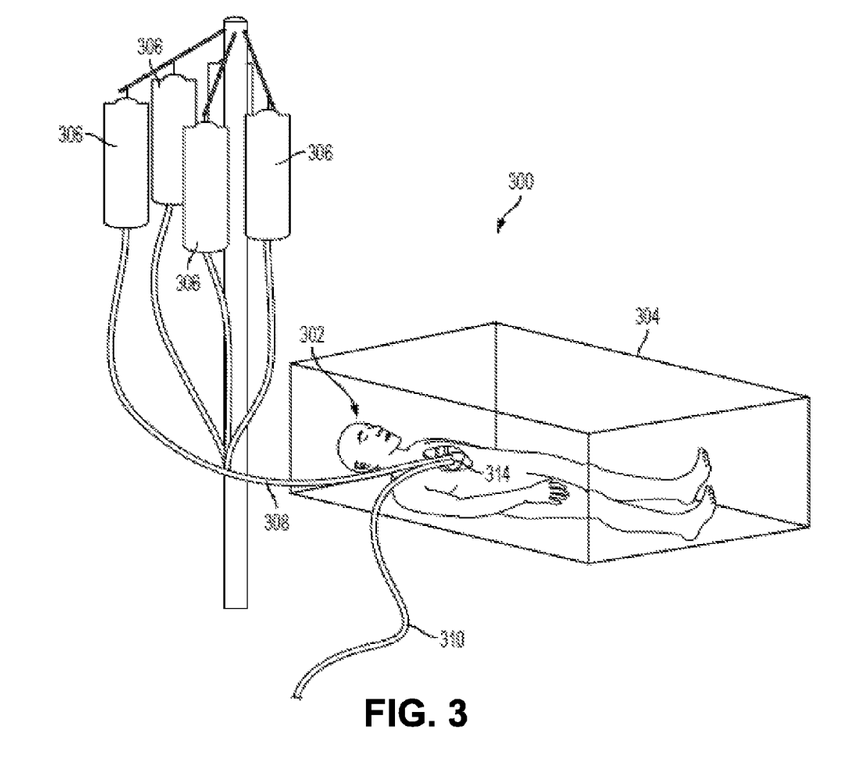
FIG. 3 is a schematic diagram showing an arrangement for perfusion of a body according to one or more embodiments of the disclosed subject matter.

In one or more embodiments, the fixation, flushing, and dehydration components of the above noted process can be performed using a single apparatus while the critical point drying is performed using a separate apparatus. For example, FIG. 3 shows an embodiment of a gravity perfusion setup 300 that can be used to perform the fixation, flushing, and dehydration components of the preservation process. Body 302 can be immersed in a bath 304. As described above, bath 304 can be filled with fixative, buffer, water, or alcohol, depending on the specific process step. An incision 312 can be made in the thoracic cavity of body 302 to provide access to the body's heart 314. A syringe or other fluid container 306 (such as an intravenous bag), which is filled with the fluid to be perfused, can be connected via infusion line 308 to the body's heart. The fluid in bath 304 can be the same as the fluid in container 306, i.e., fixative, buffer, water, or alcohol. Gravity causes the fluid in the container 306 to flow into the vascular system of the body via the heart, thereby displacing fluid currently in the vascular system from the body. Similarly, a drainage line 310 for removing fluid from the vascular system is connected to the body's heart. The infusion line 308 can have a needle or cannula, which serves as inlet flow path, connected to the left ventricle of the heart. Drainage line 310 can also have a needle or cannula, which serves as an outlet flow path, connected to the right ventricle of the heart.

In an alternative, the perfusion flow paths can be coupled to the vascular system through one or more blood-line accesses in the body's surface. For example, perfusion can be achieved by injection through the right common carotid artery with fluid being drained through the right jugular vein. For cases where damage or clotting has compromised the ability of the vascular system to adequately distribute fluid throughout the body, multiple access sites can be used. For example, multiple injections can be made through the two iliac or femoral arteries, subclavian or axillary vessels, and common carotids. Of course, other access points for introducing fluid into and removing fluid from the vascular system of the body are also possible according to one or more contemplated embodiments.

Figure 4:
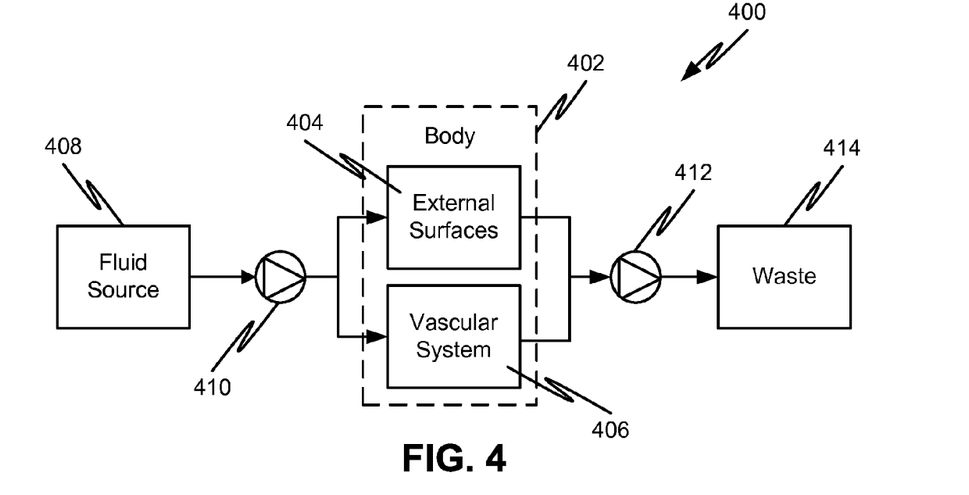
FIG. 4 is a schematic diagram of a system for perfusion of a body according to one or more embodiments of the disclosed subject matter.

While gravity perfusion provides a low-cost option for introducing fluids into the vascular system of a body, perfusion systems with manually or automatically controllable pumps may provide better and more repeatable control of perfusion. In addition, multiple perfusion fluids (e.g., fixative, buffer, water, and alcohol) can be integrated into a single setup to allow seamless and automatic transition between the preservation steps. A schematic of such a perfusion system 400 is shown in FIG. 4.

Perfusion system 400 includes a fluid source 408, which can include separate sources for each of the fluids used in preservation of the body. Alternatively, the fluid source 408 can be a single source of fluid, which is replaced for each phase of the preservation process. A pump 410 controls infusion of the fluid source into a body 402. Fluid from the fluid source 408 can be provided to the vascular system 406 of the body 402. In addition, the pump 410 can provide the fluid from the fluid source to the external surfaces 404 of the body 402. External surfaces 404 of the body 402 can include the epithelial cells of the integumentary system (such as the external facing skins cells) as well as the epithelial cells of the gastrointestinal tract.

The pump 410 can be connected to an inlet of a bath in which the body 402 is submerged. A pump 412 can also be provided to assist in the removal of fluid from the body 402 and/or bath. For example, pump 412 can remove fluid from the vascular system 406 to waste 414. Pump 412 can also be connected to an outlet of a bath in which the body 402. Pumps 410 and 412, acting separately or together, can thus continuously exchange fluid within and in contact with the body with fresh or new fluid from the fluid source. Pumps 410 and 412 can be, for example, an infusion pump, a peristaltic pump, a syringe pump, or any other known pump. Of course, pump 410 or pump 412 may be omitted and/or other pumps may be added to achieve similar fluid flow configurations according to one or more contemplated embodiments.

Figure 5A:
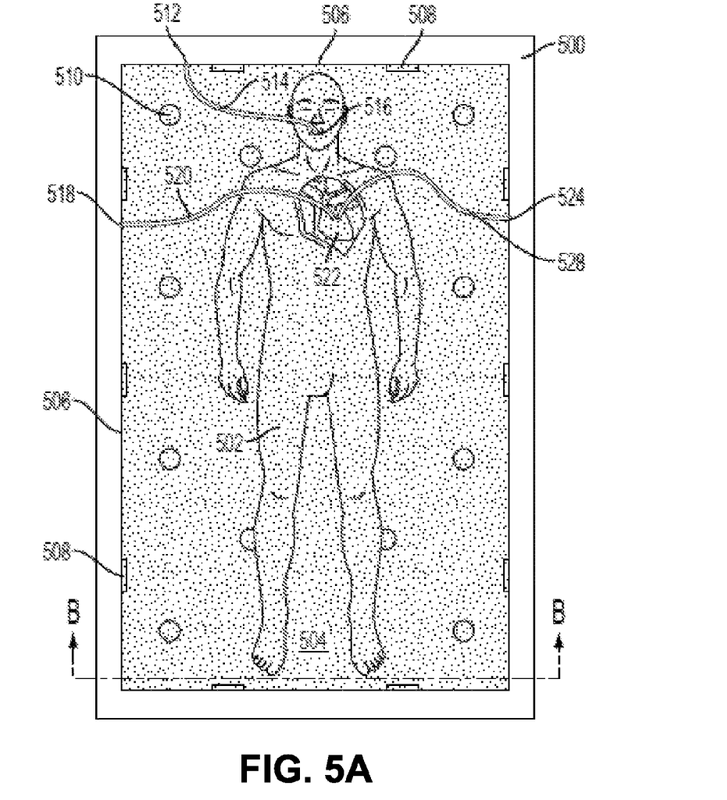
FIG. 5A is a plan view of a chamber for preserving a body according to one or more embodiments of the disclosed subject matter.
Figure 5B:
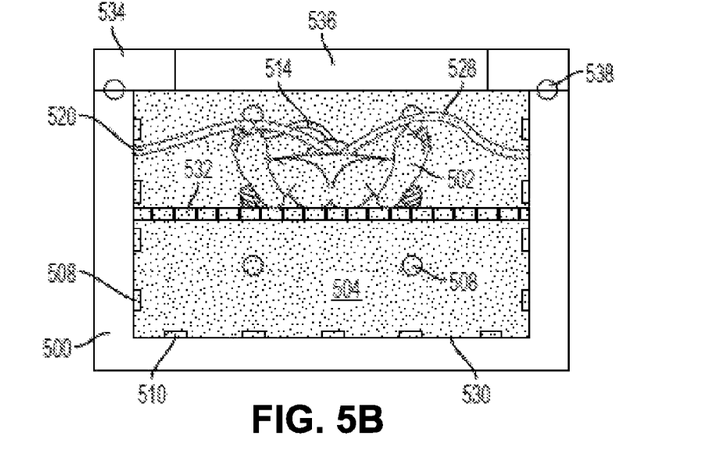
FIG. 5B is a cross-sectional view of the chamber of FIG. 5A along line B-B.

Referring now to FIGS. 5A-5B, an embodiment of a pressure chamber 500 for critical point drying of a body is shown. Pressure chamber 500 is shown in plan (i.e., top down) view in FIG. 5A and in cross-section along line B-B in FIG. 5B. Pressure chamber 500 includes multiple sidewalls 506, a bottom wall 530, and a top access panel 534. Access panel 534 (not show in FIG. 5A) can include a viewing window 536 so that an operator can monitor the critical point drying process. An O-ring 538 can extend around the perimeter of the access panel 534 so as to provide a seal. Various mechanisms (not shown) can be employed to secure the panel 534 to the side walls 506 of the pressure chamber 500.

The pressure chamber 500 can include at least two fluid ports 508, which can serve as an inlet or an outlet. Fluid ports 508 can be provided in one or more of the sidewalls 506. Alternatively or additionally, the pressure chamber 500 can include one or more fluid ports 510, which can serve as an inlet or an outlet. Fluid ports 510 can be provided in the bottom wall 530. The side walls 506 together with the bottom wall 530 and the top panel 534 define an internal volume 504, in which the body 502 is placed. Fluid (e.g., carbon dioxide) can be introduced into the volume 504 through one or more fluid ports 508/510 acting as inlets and can be removed from the volume 504 through one or more fluid ports 508/510 acting as outlets. The volume 504 is sized and shaped to accommodate the body to be preserved plus a certain volume of fluid (e.g., carbon dioxide). When the body 502 is a human body, the internal volume 504 may be between 100 L and 600 L. With such a large volume, multiple ports 508/510 can be provided in the respective sidewalls 506 and bottom wall 530 to allow efficient introduction and removal of carbon dioxide and other fluids.

An inlet connection 518 can also be provided in the interior volume for connecting an infusion line 520 (i.e., vascular inlet line) for introducing fluid (e.g., carbon dioxide) into the vascular system of the body 502. The infusion line 520 may be connected to the heart 522 of the body, for example, through the left ventricle. Similarly, an optional outlet connection 524 can also be provided in the interior volume for connecting a discharge line 528 for removing fluid from the vascular system. The discharge line 528 can be connected to the heart 522 of the body, for example, through the right ventricle. However, the discharge line 528 need not be connected to a separate outlet 524, but can discharge directly into the interior volume 504. Alternatively, the discharge line can be omitted in favor of a direct discharge from the vascular system into the interior volume. As explained above, the connection to the vascular system is not required to be through the heart. Rather, other connections, such as through arterial and venous access points on the exterior of the body, are also possible. Where more than one access point is used, more than one infusion line 520 with respective inlet 518 or more than one discharge line 528 with respective outlet 524 can be provided in the pressure chamber 500.

Pressure chamber 500 can also include one or more additional fluid lines for infusing fluid (e.g., carbon dioxide) through generally inaccessible portions of the body. For example, when connection to the vascular system is provided through the heart, the incision in the thoracic cavity can be left open such that fluid exchange between the thoracic and peritoneal cavities and the internal volume of the pressure chamber is possible. However, when connection to the vascular system is provided through arterial or venous accesses, separate fluid lines may be necessary to allow fluid (e.g., carbon dioxide) introduction to and removal from the thoracic and/or peritoneal cavities. In addition, passive fluid exchange between the gastrointestinal tract and the internal volume of the pressure chamber may be insufficient. Accordingly, one or more fluid lines can be coupled to the gastrointestinal tract to flow fluid (e.g., carbon dioxide) therethrough. For example, a fluid line 514 can be connected to an inlet connection 512 in the interior volume 504 to provide fluid (e.g., carbon dioxide) to the upper gastrointestinal tract through the mouth 516 of the body 502. A separate line (not shown) can provide fluid (e.g., carbon dioxide) to the lower gastrointestinal tract through the anus of the body 502. Intermittent introduction of fluid (e.g., carbon dioxide) coupled with intermittent removal, or continuous introduction and removal of fluid (e.g., carbon dioxide) through a single connection, can be achieved using a setup similar to that employed in colon hydrotherapy.

It is desirable to circulate fluid (e.g., carbon dioxide) to all portions of the body to allow for appropriate surface treatment and removal of all previous fluids (e.g., alcohol). A support 532 can be provided to raise the body 502 off of the bottom wall 530 and to an intermediate height within the interior volume 504. The support 532 can include holes, openings, dimples, or flow channels, or be substantially porous so as to allow fluid to reach substantially all points on the exterior surface of the body 502. For example, the support 532 can be a porous wire mesh. Other supports that allow the fluids to reach substantially all surfaces of the body 502 are also possible according to one or more contemplated embodiments.

It should be noted that the pressure chamber illustrated in FIGS. 5A-5B is not restricted to use in the critical point drying component of the preservation process. Rather, it may be used to perform the fixation, flushing, and dehydration components in addition to the critical point drying component of the preservation process, as discussed with respect to FIGS. 6 and 7A-7C below.

Figure 6:
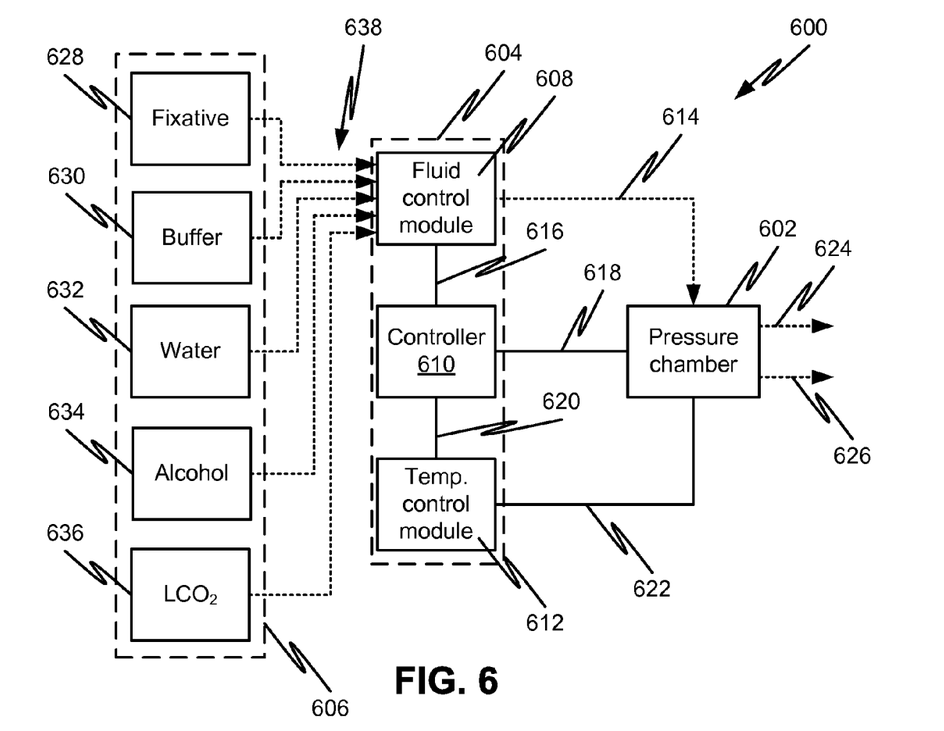
FIG. 6 is a schematic diagram of a system for in situ tissue preservation according to one or more embodiments of the disclosed subject matter.

Referring now to FIG. 6, a schematic diagram of an automated system 600 for preservation of a body is shown. The automated system 600 can include a pressure chamber 602, a control system 604, and a fluid supply system 606. Pressure chamber 602 can be substantially similar to that presented in FIGS. 5A-5B and discussed in detail above. In general, the pressure chamber 602 can be sized and shaped to accommodate a desired body size or range of body sizes.

Fluid supply system 606 can include one or more fluid containers with appropriate solutions for performing the preservation process described herein. For example, the fluid supply system 606 can include supplies of fixative 628, buffer 630, water 632, alcohol 634, and/or liquid carbon dioxide 636. Appropriate fluidic connections 638 can couple the fluid supply system, and the individual supplies therein, to the fluid control module 608 of the control system 604.

Control system 604 can include multiple control modules. For example, control system 604 can include a fluid control module 608, a central control module 610, and/or a temperature control module 612. Although shown as separate modules 608-612, the control modules of the control system 604 can be embodied in a single unit, such as a specialized computer or processor. In addition, although the control modules 608-612 are illustrated as part of a single control system 604, they can be embodied as completely separate and individual units. Each module 608-612 can be a stand-alone computer or processor or integrated with other components. For example, temperature control module 612 can be integrated with a heating and cooling system that provides the necessary temperature adjustment of the pressure chamber 602. In another example, fluid control module 608 can be integrated with a fluid pump or valve system that provides control over the fluid delivered to the pressure chamber 602. In such configurations, the central control module 610 can communicate with fluid control module 608 and temperature control module 612 through wired or wireless connections to provide control of the pressure chamber 602 environment during the preservation process.

The fluid control module 608 can include pumps and/or valves to control the flow of fluid from the fluid source 606 to the pressure chamber 602. For example, the fluid control module 608 can select the appropriate fluid supply 628-636 in the fluid supply 606 and, through appropriate control of any valves and pumps, can convey the selected fluid along input line 614 to the pressure chamber. Fluid control module 608 can also monitor the waste line 626 and/or the vent line 624 of the pressure chamber 602 in order to control flow therethrough. For example, the fluid control module 608 can regulate the flow of gaseous carbon dioxide exhaust through the vent line 624 to prevent undesirable condensation in the pressure chamber 602 after the heating step.

Temperature control module 612 can include appropriate heating or cooling elements, such as resistive heaters, thermoelectric coolers, refrigeration elements, and temperature sensors, such as thermocouples, thermoresistors, or infrared detectors, to control the temperature of the fluid in the pressure chamber 602. Alternatively, appropriate heating/cooling elements and sensors can be integrated with the pressure chamber 602 and communicate with the temperature control module through data line 622. For example, the temperature control module 612 can cool the pressure chamber 602 prior to and during the introduction of liquid carbon dioxide. The liquid carbon dioxide can be used to assist in cooling the pressure chamber. In addition, the temperature control module 612 can heat the pressure chamber 602 with the liquid carbon dioxide therein to the critical point. The temperature control module 612 can also control the temperature in the pressure chamber during other aspects of the preservation process, such as cooling the pressure chamber during the fixation procedure when the progression of decay can be inhibited by the reduced temperature.

Central control module 610 can regulate operation of the fluid control module 608 through data line 616 and the temperature control module 612 through data line 620 to perform the preservation process described above with respect to FIGS. 2A-2B. Control module 610 can also communicate with the pressure chamber 602 via data line 602, for example, to monitor the condition of the pressure chamber. For example, the control module 610 can halt or interrupt the preservation process if a sensor on the pressure chamber 602 indicates that an access panel has been opened or that a connection to the vascular system has been disturbed. Central control module 610 can also respond to inputs from an operator, for example, through a visual touch-screen display, display and keyboard, or other conventional input/output devices.

Figure 7A:
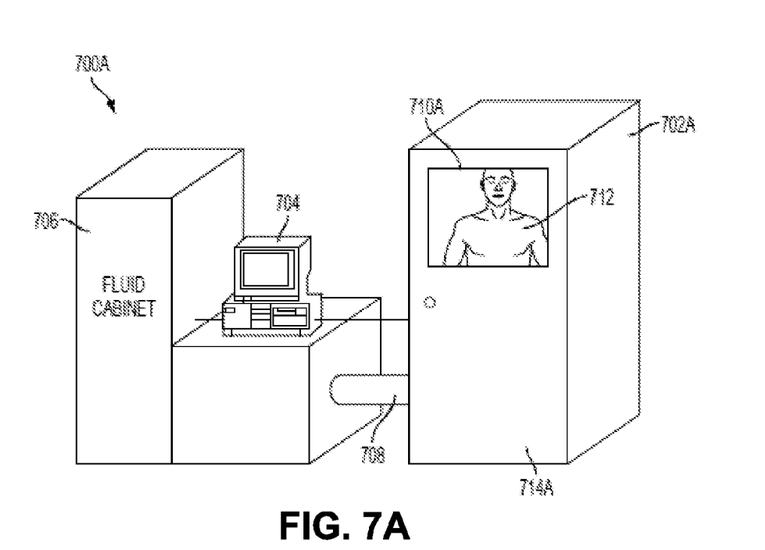
FIGS. 7A-7C show examples of various configurations for standalone preservation systems, according to one or more embodiments of the disclosed subject matter.

Referring now to FIGS. 7A-7C, embodiments of an integrated preservation system are shown. In FIG. 7A, a preservation system 700A can include a fluid cabinet 706 to supply fluid to a pressure chamber 702A. Controller 704 can control fluid flow to the pressure chamber 702A through fluid input line 708. Access panel 714A of the pressure chamber can have a window 710A for observing the body 712 during the fixation, flushing, dehydration, and critical point drying phases of the preservation process. The pressure chamber 702A can be constructed such that the body 712 is maintained upright throughout the process. Access panel 714A can be hinged and opened like a door to allow removal of the body 712 from the pressure chamber 702A.

Figure 7B:
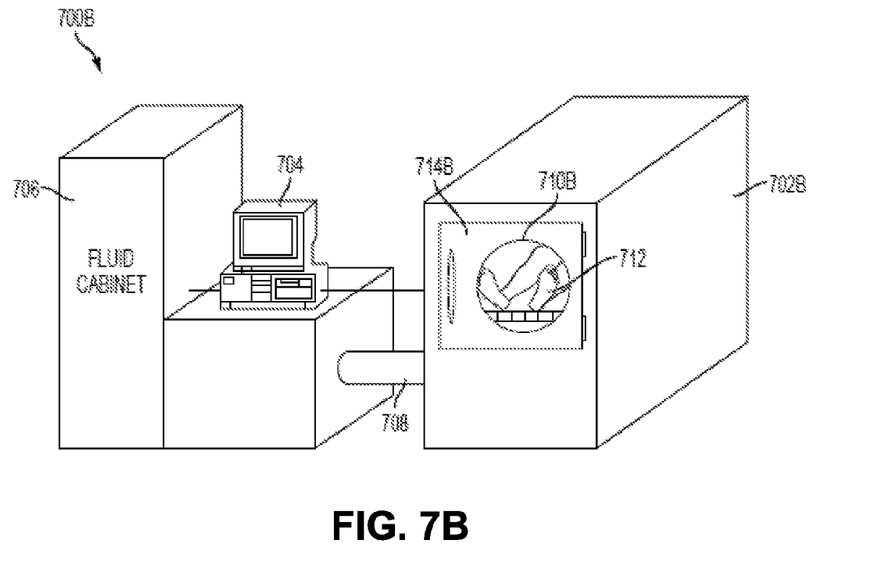

FIG. 7B illustrates an alternative preservation system 700B, which is similar to that of FIG. 7A. However, pressure chamber 702B has a horizontal configuration as opposed to the vertical configuration of chamber 702A. Body 712 can be positioned supine on a movable support, similar to storage systems in a conventional mortuary. Window 710B in access panel 714B can allow for observation of the body 712 during the fixation, flushing, dehydration, and critical point drying phases of the preservation process.

Figure 7C:
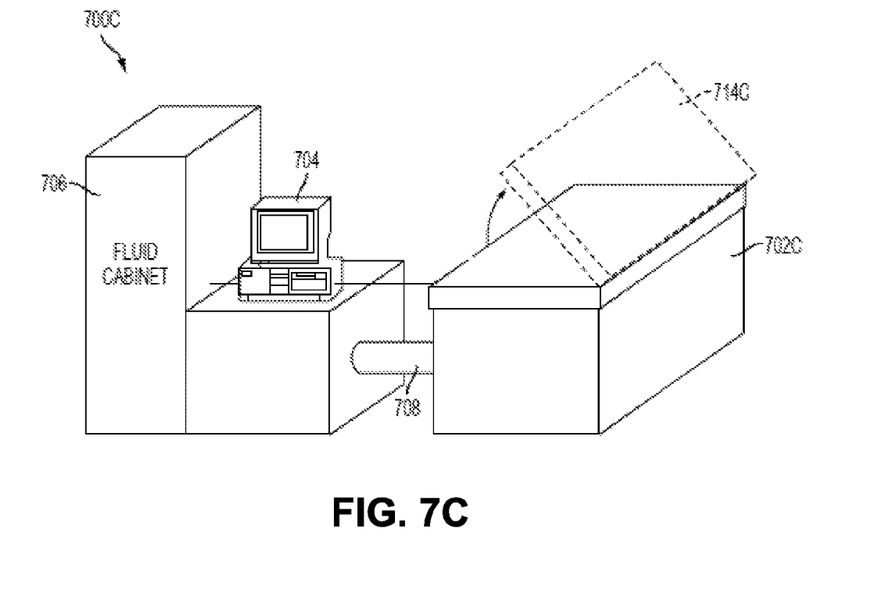

FIG. 7C illustrates yet another alternative preservation system 700C, which is similar to that of FIG. 7B. In further contrast to chamber 702B, pressure chamber 702C has the opening to the interior volume at the top thereof. Access panel 714C can rotate about a horizontal axis from a substantially horizontal position to a substantially vertical position to allow access to the interior volume and a body 712 therein. Although not shown, access panel 714C can include a window for viewing the body 712 during the fixation, flushing, dehydration, and critical point drying phases of the preservation process.

The embodiments of FIG. 7A-7C illustrate exemplary configurations for an integrated preservation system, but configurations for an integrated preservation system are not intended to be limited to these illustrated embodiments. Rather, other configurations and arrangements for an integrated preservation system are contemplated in accordance with the teachings of the present disclosure.

Figure 8:
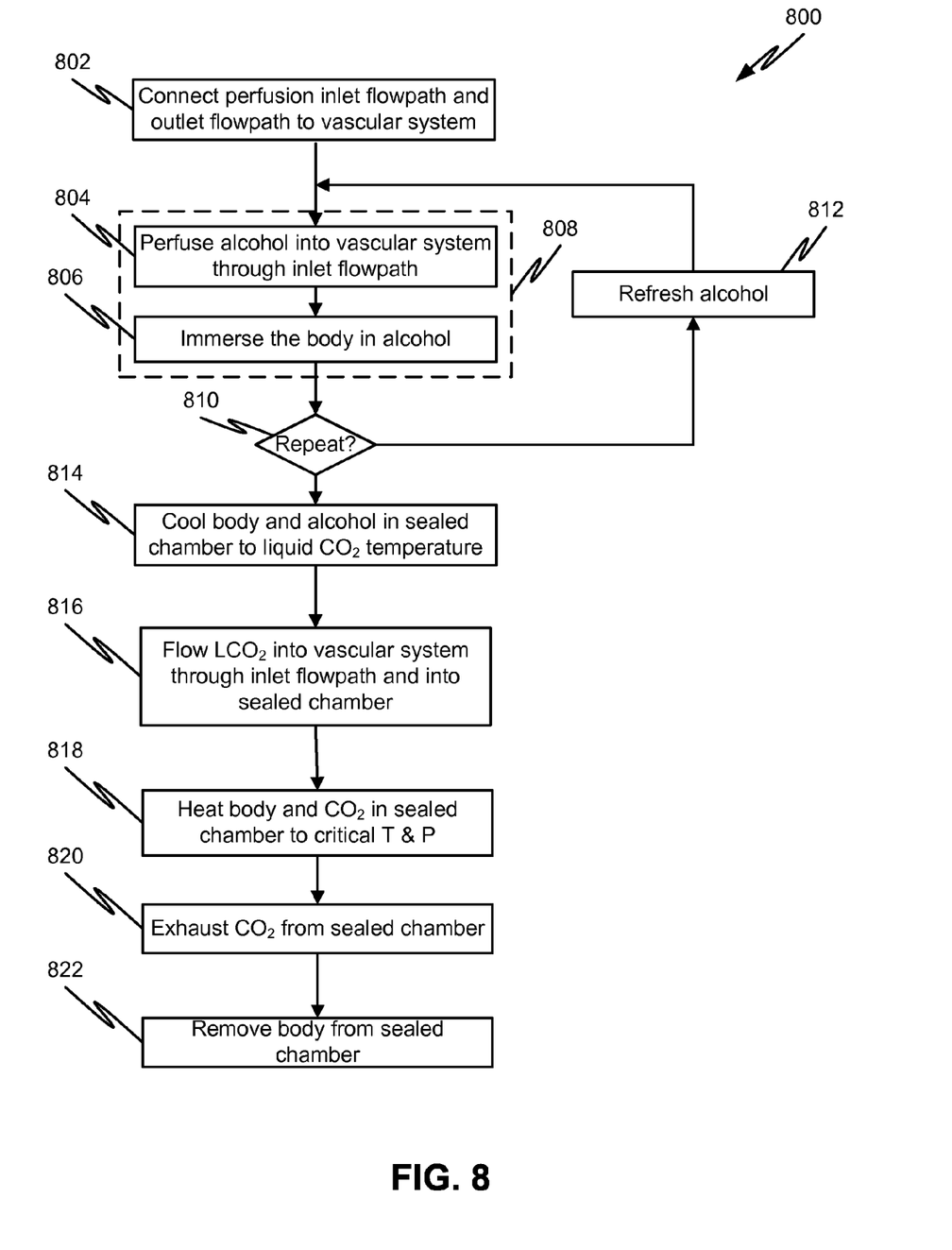
FIG. 8 is a process flow diagram of an alternative method for in situ tissue preservation according to one or more embodiments of the disclosed subject matter

As discussed above, fixation is not necessary to effect preservation of all tissue structures. Thus, the process of FIGS. 2A-2B can be modified to remove fixation steps 204-210. Alternatively, the process can be modified to perform critical point drying alone with only a dehydration step. Referring now to FIG. 8, an alternative preservation process 800 is shown. At 802, an inlet flow path and an outlet flow path can be connected to the vascular system of the body. The flow paths can include tubing and/or fluid conduits designed to carry fixative and potentially other fluids, such as buffer, water, alcohol, and liquid carbon dioxide, to the vascular system of the body. For bodies or tissues that do not have a vascular system, such as vegetation or non-vascular organisms, step 802 and the following perfusion steps may not be necessary.

At 804, the inlet and outlet flow paths can be used to perfuse an alcohol into the vascular system. For example, an alcohol, such as isopropyl alcohol (IPA) or ethanol, can be infused through the inlet flow path, while the contents of the vascular system can be drained through the outlet flow path. At least initially, blood and/or other vascular fluid will be conveyed out of the vascular system through the outlet flow path. The infusion of alcohol can continue until the contents of the vascular system are completely replaced with alcohol. The alcohol can be maintained in the vascular system for a predetermined period of time. For example, the predetermined period of time can be between one and several days, such as one day. The precise time may be a function of the size of the body, as well as other factors, and thus may be subject to variation.

At 806, the body can be immersed in a bath of alcohol for a predetermined period of time. For example, the predetermined period of time can be between one and several days. Steps 804 and 806 can be combined into a single step 808 such that the body is immersed in the bath of alcohol at the same time that alcohol flows through the vascular system. In such case, the predetermined period of time for both steps 804 and 806 can be the same. It is also noted that steps 804 and 806 can be transposed such that step 806 occurs before step 804.

It may be advantageous to renew the alcohol within and in contact with the body. Thus, steps 804 and 806 can be repeated several times (e.g., three times), each time with a new batch of alcohol maintained within and in contact with the body for a predetermined time (e.g., one day). At step 810, it is determined if steps 804 and 806 should be repeated. If so, the process proceeds to step 812, where a new batch of alcohol is prepared, and steps 804 and 806 are repeated. Otherwise, the process proceeds to 814.

At 814, the body and alcohol can be cooled in a sealed chamber to a first predetermined temperature at which a transitional fluid exists as a liquid in preparation for critical point drying. When steps 804-810 are performed using an apparatus separate from a critical point drying apparatus, the body can be transferred to the chamber in a bath of alcohol and sealed to prevent reintroduction of water. The transitional fluid can be, for example, carbon dioxide, in which case the chamber can be cooled to a temperature less than or equal to 10° C.

At 816, the inlet flow path can be used to perfuse transitional fluid into the vascular system. A common or separate inlet in the sealed chamber can be used to convey transitional fluid into the sealed chamber so as to replace the alcohol and surround the body. For example, transitional fluid, such as liquid carbon dioxide, can be infused through the inlet flow path and into the sealed chamber. The contents of the vascular system can be simultaneously drained through the outlet flow path. Since the body is located in a sealed chamber the outlet flow path can empty directly into the sealed chamber or be connected to an outlet of the sealed chamber. An outlet in the sealed chamber can serve to remove the fluid contents of the sealed chamber as fluid is added thereto.

The infusion of liquid carbon dioxide continues at least until the contents of the vascular system are completely replaced with liquid carbon dioxide. The liquid carbon dioxide can be maintained in the sealed chamber and the vascular system for a predetermined period of time. Alternatively, the liquid carbon dioxide can be continuously flowed through the sealed chamber and the vascular system for a predetermined period of time. For example, the predetermined period of time can be between ten minutes and one hour. The precise time may be a function of the size of the body, as well as other factors, and thus may be subject to variation.

At 818, the flow of liquid carbon dioxide through the sealed chamber and vascular system can be stopped such that the sealed chamber and vascular system are filled with liquid carbon dioxide. The body and the carbon dioxide in the sealed chamber can then be heated to or beyond the critical point. At 820, the pressurized carbon dioxide in the sealed chamber can be removed. Because of the relatively high pressure, the carbon dioxide can be slowly vented from the sealed chamber while maintaining the temperature above 31° C. to avoid condensation of the carbon dioxide. For example, the chamber can be vented such that the carbon dioxide is exhausted at a rate of between 8 SCFH and 10 SCFH. At pressures below 400 psi, for example, the exhaust rate can be increased, if desired. When the pressure in the sealed chamber is substantially equal to atmospheric pressure, the process proceeds to 822, wherein the preserved body can be removed from the sealed chamber.

As decomposition begins immediately upon death, it may be preferable that the methods disclosed herein be applied as soon after death as possible. For example, a recently-deceased body may be perfused within 15 minutes of death. Such a time period may be necessary when it is desired to preserve cell structure for clinical or medical examination, research, or reanimation preservation. For purely funereal and cosmetic applications where it may not be necessary to maintain all cell structure or integrity, a recently-deceased body may be perfused within 5 hours of death. Of course, these time figures are exemplary and variations therefrom are contemplated. For example, the maximum time before perfusion may be affected by the environment in which the body is maintained, as heat, humidity, and exposure to bacteria or scavengers may accelerate decomposition.

Although particular configurations have been discussed herein, other configurations can also be employed. Moreover, although specific chemicals have been discussed, other chemicals may be used to achieve the desired effect. For example, other fixatives, such as, but not limited to, formaldehyde, paraformaldehyde, osmium tetroxide, uranyl acetate, acrolein, glutaraldehyde, and combinations thereof as well as purified versions thereof are possible according to contemplated embodiments of the disclosed subject matter. In another example, other transitional fluids, such as, but not limited to, hydrogen, oxygen, nitrogen, and carbon monoxide, are also possible according to contemplated embodiments of the disclosed subject matter.

All chemicals and compositions described herein are for illustration purposes only and should not be understood as limiting of the embodiments of the disclosed subject matter. Furthermore, the foregoing descriptions apply, in some cases, to examples generated in a laboratory, but these examples can be extended to production techniques. For example, where quantities and techniques apply to the laboratory examples, they should not be understood as limiting.

It is, thus, apparent that there is provided, in accordance with the present disclosure, critical point drying systems and methods for in situ tissue preservation. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A preservation system comprising: a chamber having at least one fluid inlet and an internal volume, the chamber being sized and shaped to allow a body or an organ to be enclosed in the internal volume; a vascular inlet line comprising a needle or cannula, the needle or cannula being constructed for insertion into a portion of a vascular system of the body or the organ; a flow module configured to sequentially deliver at least fixative and liquid carbon dioxide to the chamber through the at least one fluid inlet and to the vascular system through the vascular inlet line; a temperature module configured to control a temperature of the internal volume of the chamber; and a system controller programmed to: control the flow module to fill the chamber and the vascular system with fixative, control the flow module during the filling with fixative such that external surfaces of the body or organ are exposed to the flowing fixative at a same time as the vascular system is exposed to the flowing fixative, control the flow module to fill the chamber and the vascular system with liquid carbon dioxide after the filling with the fixative, and control the temperature module to cool the internal volume to a temperature less than or equal to 10° C. prior to and during the filling with the liquid carbon dioxide.

2. The system of claim 1, wherein the system controller is further configured to, after the filling with the liquid carbon dioxide, heat the liquid carbon dioxide in the chamber and the vascular system above the carbon dioxide critical point temperature and pressure, and the chamber is constructed to withstand a temperature and a pressure of at least said carbon dioxide critical point temperature and pressure.

3. The system of claim 1, wherein the chamber has a volume of at least 100 L.

4. The system of claim 1, further comprising a support within the chamber that holds the body or the organ suspended within said chamber such that fluid can reach one or more surfaces of the body or the organ facing said support.

5. The system of claim 4, wherein the support comprises a porous wire mesh.

6. The system of claim 1, wherein
the flow module is further configured to sequentially deliver at least buffer and alcohol to the chamber through the at least one fluid inlet and to the vascular system through the vascular inlet line, and
the system controller is further programmed to:
control the flow module to fill the chamber and the vascular system with the buffer after the filling with the fixative, and
control the flow module to fill the chamber and the vascular system with the alcohol after the filling with the buffer and prior to the filling with the liquid carbon dioxide.

7. A preservation system comprising: a pressure chamber comprising at least one fluid inlet, an inlet connection, and an internal volume, the chamber being sized and shaped to allow a body or an organ to be enclosed in the internal volume, each of the at least one fluid inlet and the inlet connection being in a wall of the pressure chamber bounding the internal volume; a vascular inlet line comprising a fluid conduit and a needle or cannula at an outlet end of the fluid conduit, an inlet end of the fluid conduit being coupled to said inlet connection, the needle or the cannula being constructed for insertion into a portion of a vascular system of the body or the organ, the vascular inlet line being disposed within said internal volume; a flow module configured to separately supply at least fixative and liquid carbon dioxide to the pressure chamber through the at least one fluid inlet and to the vascular system through the vascular inlet line; a temperature module configured to control a temperature of the pressure chamber; and a system controller programmed to: control the flow module to fill the internal volume of the pressure chamber and the vascular system with fixative, control the flow module during the filling with fixative such that external surfaces of the body or organ are exposed to the flowing fixative at a same time as the vascular system is exposed to the flowing fixative, control the flow module to fill the internal volume of the pressure chamber and the vascular system with liquid carbon dioxide after the filling with fixative, and after the filling with the liquid carbon dioxide, control the temperature module, to heat the liquid carbon dioxide in the internal volume of the pressure chamber and the vascular system above the carbon dioxide critical point temperature and pressure, wherein the pressure chamber is constructed to withstand a temperature and a pressure of at least said carbon dioxide critical point temperature and pressure.

8. The system of claim 7, wherein the system controller is further configured to control the temperature module to cool the internal volume to a temperature below or equal to 10° C. prior to the filling with liquid carbon dioxide.

9. The system of claim 7, wherein the pressure chamber has a volume of at least 100 L.

10. The system of claim 7, further comprising a support within the pressure chamber that holds the body or the organ suspended within said pressure chamber such that fluid can reach one or more surfaces of the body or the organ facing said support.

11. The system of claim 7, further comprising a fixative source, a buffer source, an alcohol source, and a liquid carbon dioxide source, each of the sources being coupled to the flow module, the flow module being configured to sequentially deliver fluid from each of the sources to fill the pressure chamber and the vascular system.

12. The system of claim 7, wherein the pressure chamber comprises a wall with an inlet connection, the inlet connection being coupled to an inlet end of the fluid conduit of the vascular inlet line within the internal volume.

\* \* \* \* \*